US010279744B2

(12) United States Patent
Hirano et al.

(10) Patent No.: US 10,279,744 B2
(45) Date of Patent: May 7, 2019

(54) MIRROR-ATTACHED IMAGING APPARATUS

(71) Applicant: KYOCERA Corporation, Kyoto-shi, Kyoto (JP)

(72) Inventors: Arata Hirano, Yokohama (JP); Woojung Kim, Yokosuka (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/770,451

(22) PCT Filed: Oct. 27, 2016

(86) PCT No.: PCT/JP2016/004732
§ 371 (c)(1),
(2) Date: Apr. 23, 2018

(87) PCT Pub. No.: WO2017/073064
PCT Pub. Date: May 4, 2017

(65) Prior Publication Data
US 2018/0312113 A1  Nov. 1, 2018

(30) Foreign Application Priority Data

Oct. 27, 2015  (JP) .................. 2015-211072

(51) Int. Cl.
G08B 23/00 (2006.01)
B60R 1/04 (2006.01)
(Continued)

(52) U.S. Cl.
CPC ................. *B60R 1/04* (2013.01); *A61B 5/18* (2013.01); *B60R 1/12* (2013.01); *B60R 11/04* (2013.01);
(Continued)

(58) Field of Classification Search
CPC .. B60R 1/04; B60R 1/12; B60R 11/04; A61B 5/18; A61B 5/6893; A61B 2503/22; G08B 21/06; G03B 15/00; H04N 7/18
(Continued)

(56) References Cited

U.S. PATENT DOCUMENTS 6,140,933 A * 10/2000 Bugno ...................... B60R 1/12
33/333
6,304,187 B1  10/2001 Pirim
(Continued)

FOREIGN PATENT DOCUMENTS

JP  S60-214691 A  10/1985
JP  2000-264128 A  9/2000
(Continued)

Primary Examiner — Kerri L McNally
Assistant Examiner — Thang D Tran
(74) Attorney, Agent, or Firm — Procopio Cory Hargreaves and Savitch LLP

(57) ABSTRACT

A mirror-attached imaging apparatus includes a semi-transmissive mirror through which at least some incident light can pass, an camera configured to capture a subject by receiving light passing through the semi-transmissive mirror, and a support configured to attach the semi-transmissive mirror and the camera to a vehicle body. The semi-transmissive mirror is movable relative to the support, and the camera is attached to the support.

3 Claims, 4 Drawing Sheets

(51) Int. Cl.
   *B60R 1/12*    (2006.01)
   *B60R 11/04*   (2006.01)
   *G03B 15/00*   (2006.01)
   *H04N 7/18*    (2006.01)
   *A61B 5/18*    (2006.01)
   *G08B 21/06*   (2006.01)
   *A61B 5/00*    (2006.01)

(52) U.S. Cl.
   CPC ............. *G03B 15/00* (2013.01); *G08B 21/06* (2013.01); *H04N 7/18* (2013.01); *H04N 7/183* (2013.01); *A61B 5/6893* (2013.01); *A61B 2503/22* (2013.01)

(58) Field of Classification Search
   USPC ........................................................ 340/576
   See application file for complete search history.

(56) References Cited

U.S. PATENT DOCUMENTS

| | | | |
|---|---|---|---|
| 6,717,518 | B1 | 4/2004 | Pirim et al. |
| 9,396,857 | B2 | 7/2016 | Kinoshita et al. |
| 2002/0003571 | A1* | 1/2002 | Schofield ................ B60C 23/00 348/148 |
| 2002/0159270 | A1* | 10/2002 | Lynam .................... B60K 35/00 362/492 |
| 2003/0112536 | A1* | 6/2003 | Wachi ...................... B60R 1/04 359/880 |
| 2004/0095651 | A1* | 5/2004 | Aoki .................. G02B 27/0101 359/630 |
| 2006/0061008 | A1* | 3/2006 | Kamer ................ B29C 45/0017 264/250 |
| 2006/0164230 | A1* | 7/2006 | Dewind ................ B60K 35/00 340/461 |
| 2008/0075442 | A1* | 3/2008 | Yamashita ............. B60R 11/04 396/25 |
| 2009/0002575 | A1* | 1/2009 | Yamada .................... B60R 1/04 349/1 |
| 2010/0277637 | A1* | 11/2010 | Katsuda ............... G02B 5/0833 348/335 |
| 2011/0317015 | A1* | 12/2011 | Seto .......................... B60R 1/00 348/148 |
| 2012/0062743 | A1* | 3/2012 | Lynam ................... B60Q 9/005 348/148 |
| 2013/0293713 | A1* | 11/2013 | Scudder .................. B60R 11/04 348/148 |
| 2014/0055617 | A1* | 2/2014 | Minikey, Jr. .............. B60R 1/04 348/148 |
| 2014/0125436 | A1 | 5/2014 | Kinoshita et al. |
| 2014/0347488 | A1* | 11/2014 | Tazaki ..................... B60R 1/04 348/148 |
| 2015/0085121 | A1* | 3/2015 | Englander .............. H04N 7/183 348/148 |
| 2015/0146051 | A1* | 5/2015 | Abe ...................... H04N 5/2254 348/262 |
| 2016/0337594 | A1* | 11/2016 | Morishita .............. B60K 35/00 |
| 2017/0140699 | A1* | 5/2017 | Okohira ................... B60R 1/00 |

FOREIGN PATENT DOCUMENTS

| | | |
|---|---|---|
| JP | 2002-509321 A | 3/2002 |
| JP | 2002-316580 A | 10/2002 |
| JP | 2008-290545 A | 12/2008 |
| JP | 2010-006362 A | 1/2010 |
| JP | 2014-112541 A | 6/2014 |
| JP | 2015-228284 A | 12/2015 |

* cited by examiner

MIRROR-ATTACHED IMAGING APPARATUS

CROSS REFERENCE TO RELATED APPLICATION

This application claims priority to and the benefit of Japanese Patent Application No. 2015-211072 filed on Oct. 27, 2015, the entire contents of which are incorporated herein by reference.

TECHNICAL FIELD

The present disclosure relates to a mirror-attached imaging apparatus.

BACKGROUND

Recently, camera apparatuses mounted in vehicles such as automobiles have been used to detect the status of a driver, such as falling asleep or looking away, by imaging the driver.

Considering the internal appearance of the vehicle, it is desirable that such camera apparatuses are mounted at a position that is not noticeable to occupants of the vehicle.

CITATION LIST

Patent Literature

SUMMARY

A mirror-attached imaging apparatus according to the present disclosure includes a semi-transmissive mirror, a camera, and a support. The semi-transmissive mirror allows at least some incident light to pass therethrough. The camera captures a subject by receiving light passing through the semi-transmissive mirror. The support attaches the semi-transmissive mirror and the camera to a vehicle body. The semi-transmissive mirror is movable relative to the support, and the camera is attached to the support.

BRIEF DESCRIPTION OF THE DRAWINGS

In the accompanying drawings:

FIGS. 2A to 2C are diagrams illustrating the mirror-attached imaging apparatus illustrated in FIG. 1, wherein FIG. 2A is a perspective view illustrating a front side of the mirror-attached imaging apparatus, FIG. 2B is a perspective view illustrating a rear side of the mirror-attached imaging apparatus, and FIG. 2C is a perspective view illustrating an inside of the mirror-attached imaging apparatus;

DETAILED DESCRIPTION

According prior art methods, when an occupant changes the angle of a mirror, the angle of an optical axis of a camera apparatus mounted inside the mirror also changes. As a result, an imaging range of the camera apparatus changes. In this case, the camera apparatus may no longer be able to capture the driver, and thus may be unable detect a state of the driver for safe driving support.

According to the present disclosure, the imaging range of the imaging apparatus is maintained even when the angle of the mirror is changed.

Hereinafter, embodiments of the present disclosure will be described with reference to the accompanying drawings.

First Embodiment

A mirror-attached imaging apparatus 1 according to a first embodiment will be described with reference to FIG. 1.

Figure 1:
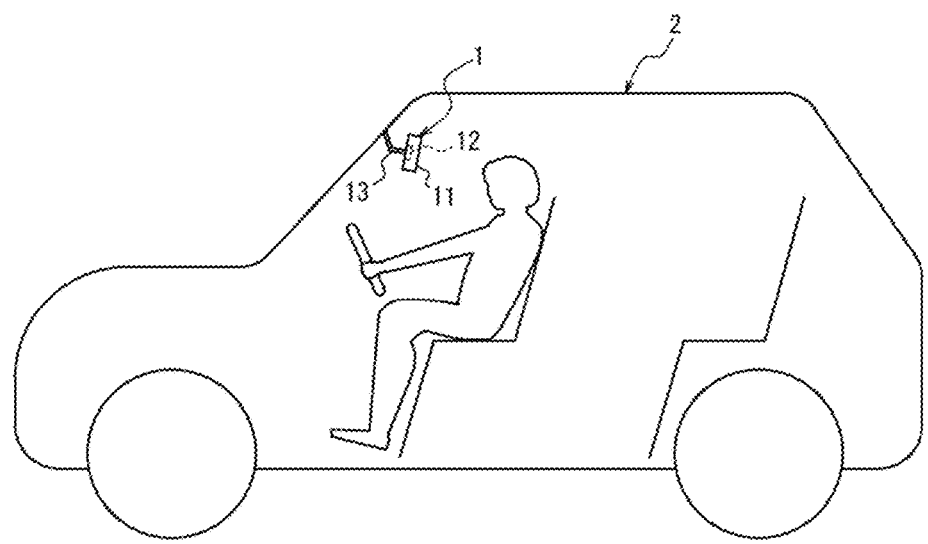
FIG. 1 is a diagram illustrating arrangement of the mirror-attached imaging apparatus inside a vehicle according to a first embodiment.

As illustrated in FIG. 1, the mirror-attached imaging apparatus 1 is located in a position inside a vehicle 2 where, for example, a rearview mirror is commonly located. The vehicle 2 is, for example, an automobile, a bus, or a truck that moves in accordance with operations performed by a driver.

The mirror-attached imaging apparatus 1 includes a mirror unit 11 and a camera unit 12 (an imaging apparatus). The mirror-attached imaging apparatus 1 is attached to a vehicle body via a support 13.

As illustrated in FIG. 1, the mirror unit 11 includes a mirror 14, via which the driver is able to check the rear or the sides of the vehicle 2. In particular, the mirror unit 11 is located in such a manner that light incident from the rear or the sides of the vehicle 2 is reflected and reaches a position where the driver's face is expected to be present when the driver is in the driver seat. Also, the mirror unit 11 is attached to the vehicle body via the support 13 in a rotatable manner relative to the support 13.

Figure 2A:
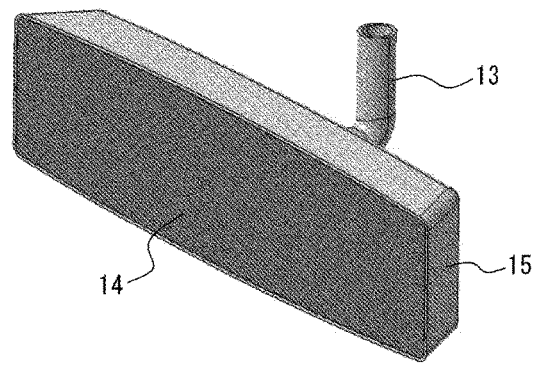
Figure 2B:
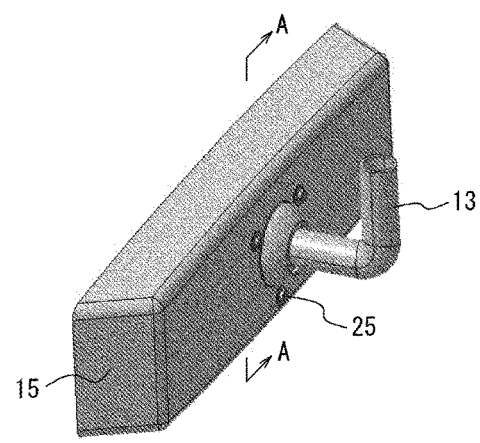
Figure 2C:
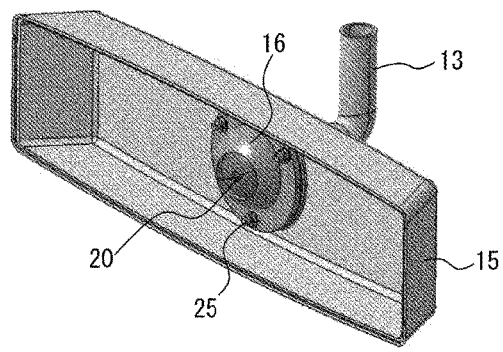

The mirror unit 11 includes at least one mirror 14 of any appropriate shape, a casing 15 (a mirror housing) as illustrated in FIG. 2A, and a camera cover 16 as illustrated in FIG. 2C. The casing 15 is attached to a rear side of the mirror 14 and constitutes, together with the mirror 14, a housing. The mirror unit 11 is attached to the support 13 in the manner illustrated in FIG. 2B. The casing 15 of the mirror unit 11 accommodates a camera unit 12 covered by the camera cover 16 illustrated in FIG. 2C.

The mirror 14 is a cold mirror for reflecting light in the visible spectrum and transmissive to light in the infrared spectrum as incident light. The mirror unit 11 is equipped with a camera module 17 (an imaging unit) having sensitivity to light in the infrared spectrum. Thus, the inside of the vehicle 2 is reflected in the mirror 14. Accordingly, the mirror-attached imaging apparatus 1 is used as a rearview mirror by the driver and other occupants of the vehicle 2. On the other hand, the camera module 17 is capable of capturing an image of the driver or other occupants inside the vehicle 2 by capturing an image of infrared light passing through the mirror 14. In some embodiments, the mirror 14 may be a half mirror, and the camera module 17 may be a visible light camera. In this case, some of the visible light as the incident light passing through the mirror 14 is captured as a visible light image by the camera module 17.

The casing 15, together with the mirror 14, constitutes a housing that includes one side formed by the mirror 14. In this case, the mirror 14 is located such that its side for reflection of visible light forms one side of the exterior of the casing. The casing 15 may be made of any appropriate material, including opaque materials. By making the casing 15 opaque, the camera unit 12 accommodated in the casing 15 becomes less visible to the occupants of the vehicle 2. This offers an advantage in that it the occupants are less conscious of being captured by the camera.

Figure 3:
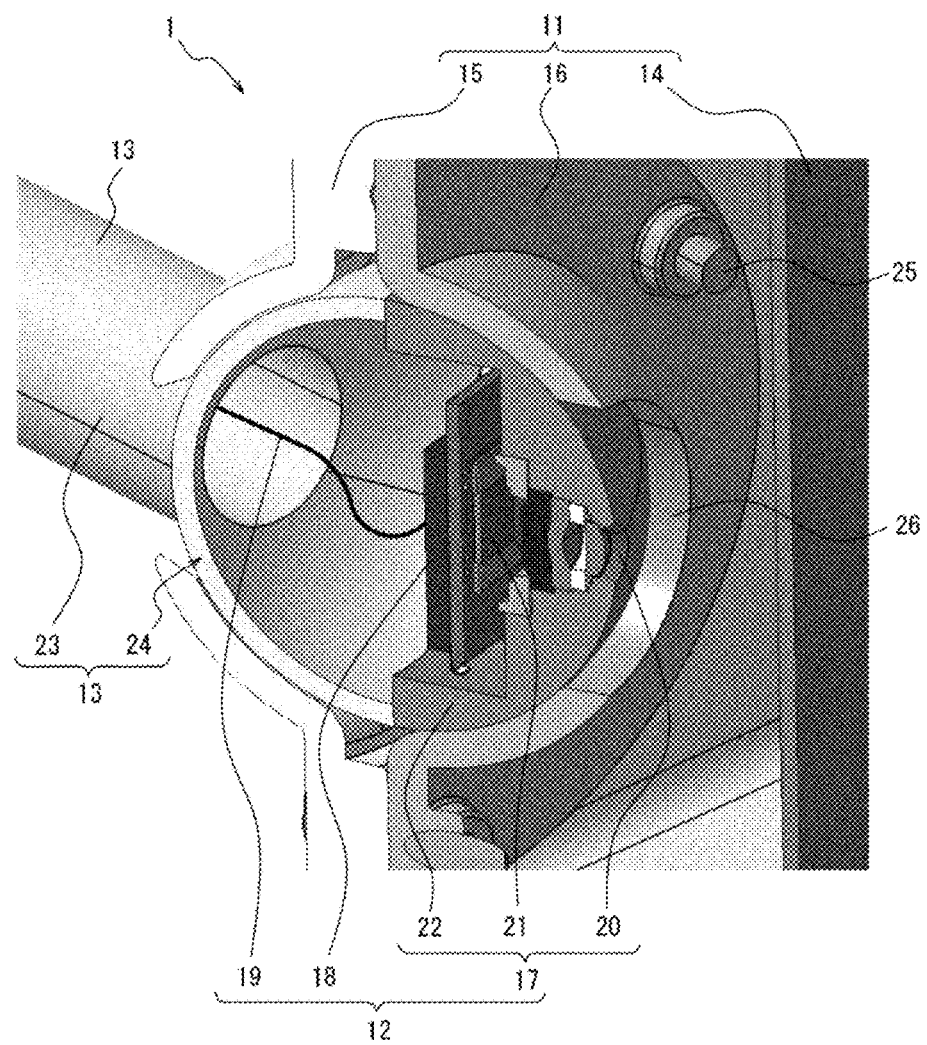
FIG. 3 is a cross-sectional view taken from line A-A of the mirror-attached imaging apparatus illustrated in FIG. 2B.

The camera cover 16 protects the camera unit 12 as illustrated in FIG. 3. The camera cover 16 is fixed by screws 25 to the rear side of the casing 15 accommodating the camera unit 12 as illustrated in FIG. 2C. The camera cover 16 includes an opening 26. The camera cover 16 opens within the mirror housing in such a manner as to avoid hindering light passing through the mirror 14 from reaching a lens unit 20, which will be described later. The opening 26 is sized to allow the lens unit 20 to receive the light in the entire movable range of the mirror unit 11 relative to the support 13.

As mentioned above, the camera unit 12 is accommodated in the casing of the mirror unit 11 and includes the camera module 17, an image output connector 18, and a harness 19 as illustrated in FIG. 3.

The camera module 17 includes a lens unit 20 configured with at least one lens, an image sensor 21, and a camera housing 22. The lens unit 20 constitutes an imaging optical system. The image sensor 21 is a CCD image sensor or a CMOS image sensor. The image sensor 21 is attached perpendicular to an optical axis of the imaging optical system configured with the lens unit 20. The camera housing 22 serves as a container for accommodating the lens unit 20 and the image sensor 21. According to the present embodiment, the exterior of the camera housing 22 is formed as a hemisphere. The camera housing 22 is formed such that the outer surface as a whole is spherical, by joining an end portion of the camera housing 22 with a joint portion 24, which will be described later.

The camera module 17 is attached to the vehicle body via the support 13 so as to be fixed to the support 13. The support 13 may be movable or fixed with respect to the vehicle body. When the support 13 is movable, the imaging range of the camera module 17 may be changed by adjusting an orientation or a length of the support 13. This adjustment enables the camera module 17 to capture the driver alone, other occupants, or a subject outside the vehicle.

The angle of view of the camera module 17 may be set to any appropriate value. For example, for capturing both the driver and a person in the passenger seat, the angle of view of the camera module 17 may be wider than the angle of view for capturing the driver alone. The angle of view may be manually set by an occupant, or set on the basis of a signal transmitted from a control apparatus or the like of the vehicle 2, or set in accordance with a predetermined environmental change.

The image output connector 18 is an interface configured to output information indicating an image captured by the camera module 17.

The harness 19 is an assembly including a cable, a wire, and the like. The cable transmits information indicating the image output from the image output connector 18 to the control apparatus and the display apparatus of the vehicle 2. The wire supplies power to the camera module 17. The harness 19 is wired through a cavity within the support 13 and contains a first end coupled to the image output connector 18 and a second end coupled to the control apparatus, the display apparatus, a communication apparatus and the like of the vehicle 2.

The support 13 is a member for attaching the mirror-attached imaging apparatus 1 to the vehicle body and includes a vehicle-side connection portion 23 and the joint portion 24. The vehicle-side connection portion 23 and the joint portion 24 are integrally formed.

The vehicle-side connection portion 23 contains one end fixedly attached to the vehicle body. In the example illustrated in FIG. 3, one end of the vehicle-side connection portion 23 is fixedly attached to the inside of the vehicle. The mirror unit 11 and the camera unit 12 of the mirror-attached imaging apparatus 1 are attached to the joint portion 24. In this way, the mirror-attached imaging apparatus 1 is mounted in the vehicle 2 via the support 13.

As mentioned above, the camera unit 12 of the mirror-attached imaging apparatus 1 is fixedly attached with respect to the joint portion 24. Here, an example of the attachment of the camera unit 12 to the joint portion 24 will be described in detail.

As illustrated in FIG. 3, the camera unit 12 is mounted in the joint portion 24, with an end of the joint portion 24 having a hemispherical form and an end of the camera housing 22 having a hemispherical exterior being joined together such that their exteriors as a whole form a sphere. That is, the joint portion 24 and the camera housing 22 together form a sphere. Thus, the camera module 17 is disposed inside the sphere. The lens unit 20 receives light passing through the mirror unit 11 without being blocked by a spherical receiving portion.

The mirror unit 11 is movably attached with respect to the joint portion 24. Here, an example of the attachment of the mirror unit 11 to the joint portion 24 will be described in detail.

As illustrated in FIG. 3, the casing 15 and the camera cover 16 of the mirror unit 11 each have partially spherical inner surface and are fixed together by the screws 25 in such a manner as to allow the sphere formed by the camera unit 12 and the joint portion 24 mentioned above to slide thereon. That is, portions of the casing 15 and the camera cover 16 of the mirror unit 11 together form the spherical receiving portion that accommodates the sphere formed by the joint portion 24 and the camera housing 22 in a rotatable manner. In this way, the mirror unit 11 containing the casing 15 is joined to the spherical receiving portion formed by the joint portion 24 and the camera cover 16 in a ball-joint manner and may rotate within a range along the outer surface thereof. Thus, the orientation of the mirror unit 11 may be changed relative to the support 13.

According to the first embodiment, as described above, in the mirror-attached imaging apparatus 1 the semi-transmissive mirror is movable relative to the support 13, while the camera module 17 (the imaging unit) of the camera unit 12 (the imaging apparatus) is fixed to the support 13. This configuration enables the imaging range to be maintained even when the angle of the mirror 14 is changed. Thus, when an occupant of the vehicle 2 changes the orientation of the mirror 14, the camera module 14 may maintain the same orientation and capture an occupant. In this way, the mirror-attached imaging apparatus 1 may continually assist the driver for safe driving by detecting, for example, the state of the driver. Also, by capturing a passenger, for example, a controller configured to control a child lock by checking characteristics of a person in a rear seat or control the air conditioning in accordance with positions of the occupants within a cabin space may continue this control even when the orientation of the mirror 14 is changed.

According to the first embodiment, the camera module 17 is accommodated in the mirror unit 11 and thus is unlikely to be touched by an object or a person. Thus, the camera module 17 may be protected. Also, accommodating the camera module 17 in the mirror unit 11 eliminates the necessity to install the imaging unit elsewhere in the vehicle 2 than the mirror unit 11, thus enabling efficient utilization of the cabin, in which space is limited.

According to the first embodiment, also, the camera module 17 is covered by the camera cover 16, and the camera cover 16 includes the opening 26. Thus, the camera module 17 other than a light receiving portion thereof may be protected. Further, the opening 26 is formed in such a manner as to avoid hindering the light from reaching the camera module 17 in the entire movable range of the mirror unit 11. Accordingly, a subject may still be captured when the orientation of the mirror 14 is changed.

Second Embodiment

Next, a second embodiment of the present disclosure will be described with reference to the accompanying drawings.

Figure 4:
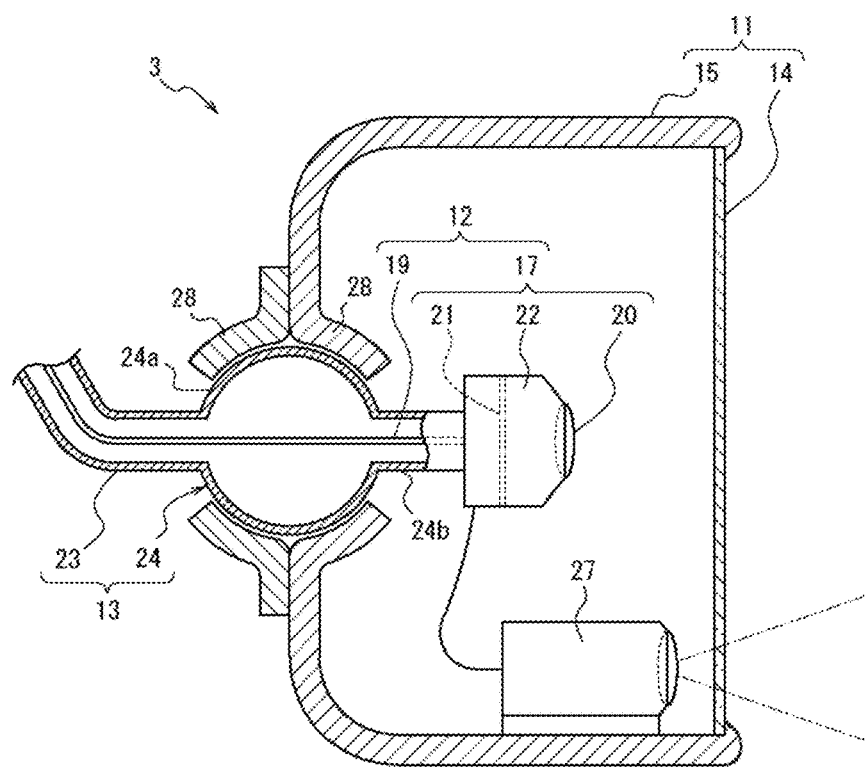
FIG. 4 is a cross-sectional view of the mirror-attached imaging apparatus according to a second embodiment.

Similarly to the mirror-attached imaging apparatus 1 according to the first embodiment, a mirror-attached imaging apparatus 3 according to the second embodiment is located at the position where the rearview mirror is commonly located in the vehicle 2. As illustrated in FIG. 4, the mirror-attached imaging apparatus 3 includes the mirror unit 11, the camera unit 12, and an illumination unit 27 (an illumination light) and is attached to the vehicle body via the support 13.

In the mirror-attached imaging apparatus 1 according to the first embodiment, the lens unit 20 and the image sensor 21 are located inside the sphere formed by the joint portion 24 and the camera housing 22. In the mirror-attached imaging apparatus 3 according to the second embodiment, on the other hand, the joint portion 24 has a spherical shape, and the lens unit 20, the image sensor 21, and the camera housing 22 are located outside the spherical shape.

Here, the mirror-attached imaging apparatus 3 according to the second embodiment will be described in detail with reference to FIG. 4. Configurations of the second embodiment similar to the first embodiment will be omitted as appropriate.

As illustrated in FIG. 4, the support 13 includes the vehicle-side connection portion 23 and the joint portion 24. The joint portion 24 includes a spherical portion 24a having a spherical shape and a camera-side connection portion 24b coupled to the camera module 17. Also, a spherical receiving portion 28 formed by a portion of the casing 15 rotatably accommodates the spherical portion 24a. The camera module 17 is located inside the mirror housing and outside the opening of the spherical receiving portion 28 via the camera-side connection portion 24b. A positional relationship between the opening of the spherical receiving portion 28 and the camera-side connection portion 24b is determined to avoid interrupting the movement of the mirror 14. The harness 19 is wired through the cavity within the support 13. The harness 19 includes the first end coupled to the image output connector 18. The harness 19 also includes the second end, opposite to the first end, coupled to the control apparatus, the display apparatus, the communication apparatus and the like of the vehicle 2.

The illumination unit 27 is located inside the mirror unit 11 and emits illumination light to the imaging range of the mirror-attached imaging apparatus 3.

According to the second embodiment, as described above, similarly to the first embodiment, the mirror-attached imaging apparatus 3 includes the semi-transmissive mirror that is movable relative to the support 13, and the camera module 17 (the imaging unit) of the camera unit 12 (the imaging apparatus) is fixed to the support 13. This configuration enables the imaging range to be maintained even when the angle of the mirror 14 is changed.

According to the second embodiment, also, similarly to the first embodiment, the camera module 17 is accommodated in the mirror unit 11. This configuration enables the camera module 17 to be prevented from being touched by an object or a person and thus protects the camera module 17. Further, the camera module 17 accommodated in the mirror unit 11 eliminates the necessity to install the imaging unit elsewhere in the vehicle 2 than the mirror unit 11, thus enabling efficient utilization of the cabin, in which space is limited.

Third Embodiment

According to the present embodiment, the joint portion 24 having a hemi-spherical form and the camera housing 22 having a hemi-spherical formed outer exterior are individual members and are joined together to form a spherical member. However, the joint portion 24 may have, for example, a spherical form to enclose the lens unit 20.

According to the present embodiment, also, the lens unit 20 is enclosed in the sphere formed by the joint portion 24 and the camera housing 22. However, the joint portion 24 may have, for example, a spherical form to enclose the camera housing 22 and the lens unit 20 accommodated in the camera housing 22.

Further, although in the above description the mirror-attached imaging apparatus 3 according to the second embodiment is provided with the illumination unit 27, the mirror-attached imaging apparatus 1 according to the first embodiment may be provided with the illumination unit 27.

REFERENCE SIGNS LIST 1, 3 mirror-attached imaging apparatus
2 vehicle
11 mirror unit
12 camera unit (imaging apparatus)
13 support
14 mirror (semi-transmissive mirror)
15 casing
16 camera cover
17 camera module (imaging unit)
18 image output connector
19 harness
20 lens unit
21 image sensor
22 camera housing
23 vehicle-side connection portion
24 joint portion
24a spherical portion
24b lens-side joint portion
25 screw
26 opening
27 illumination unit
28 spherical receiving portion

The invention claimed is:
1. A mirror-attached imaging apparatus comprising:
a semi-transmissive mirror through which at least some incident light can pass;
a camera configured to capture a subject by receiving light passing through the semi-transmissive mirror;
a support configured to attach the semi-transmissive mirror and the camera to a vehicle body;
a mirror housing containing the semi-transmissive mirror as one side of the mirror housing; and
a ball-joint including a spherical portion located at one end of the support and a spherical receiving portion containing a part of the mirror housing and configured to movably accommodate the spherical portion, the
spherical receiving portion including an opening in a
part facing the mirror,
wherein the semi-transmissive mirror is movable relative
to the support, and the camera is attached to the
support, and
wherein the camera is located inside the spherical portion
and receives the light passing through the semi-transmissive mirror via the opening of the spherical receiving portion.

2. The mirror-attached imaging apparatus according to claim 1, wherein the mirror housing includes an illumination configured to emit illumination light that passes through the semi-transmissive mirror.

3. The mirror-attached imaging apparatus according to claim 1, wherein the semi-transmissive mirror is a cold mirror, and the camera has a sensitivity to light in infrared spectrum.

* * * * *